United States Patent [19]

Bolhofer

[11] 4,055,592
[45] Oct. 25, 1977

[54] N-(SULFO-LOWER ALKYL) AMIDES OF (3-TRIFLUOROMETHYLPHENOXY) (4-CHLOROPHENYL)ACETIC ACID

[75] Inventor: William A. Bolhofer, Frederick, Pa.

[73] Assignee: Merck & Co., Inc., Rahway, N.J.

[21] Appl. No.: 657,813

[22] Filed: Feb. 13, 1976

Related U.S. Application Data

[63] Continuation of Ser. No. 501,717, Aug. 29, 1974, abandoned, which is a continuation-in-part of Ser. No. 309,569, Nov. 24, 1972, abandoned, which is a continuation-in-part of Ser. No. 232,966, March 8, 1972, Pat. No. 3,787,423.

[51] Int. Cl.$^2$ .................. A61K 31/185; C07C 143/52
[52] U.S. Cl. ..................... 260/507 R; 260/295 R; 260/307 R; 260/544 R; 260/556 A; 548/356
[58] Field of Search ............ 260/507 R, 510, 556 AC, 260/556 A, 556 F, 508, 509

[56] References Cited

U.S. PATENT DOCUMENTS

| | | | |
|---|---|---|---|
| 3,787,423 | 1/1974 | Bolhofer | 260/295.5 R |
| 3,789,068 | 1/1974 | Ito et al. | 260/507 R |

OTHER PUBLICATIONS

Bolhofer, Chemical Abstracts, vol. 79, p. 354, No. 136580r (1973).

*Primary Examiner*—Floyd D. Higel
*Attorney, Agent, or Firm*—Walter Patton; Richard A. Thompson

[57] ABSTRACT

N-(Sulfo-lower alkyl)amides of (3-trifluoromethylphenoxy)-(4-chlorophenyl)acetic acid which are useful in the treatment of atherosclerosis. The N-(sulfo-lower alkyl)amides of (3-trifluoromethylphenoxy) (4-chlorophenyl)-acetic acid are prepared by reacting a (3-trifluoromethylphenoxy) (4-chlorophenyl)acetyl halide with an amino-lower alkanesulfonic acid.

3 Claims, No Drawings

N-(SULFO-LOWER ALKYL) AMIDES OF (3-TRIFLUOROMETHYLPHENOXY) (4-CHLOROPHENYL)ACETIC ACID

This application is a continuation of U.S. application Ser. No. 501,717, filed Aug. 29, 1974, now abandoned, which is a continuation-in-part application of the copending application Ser. No. 309,569, filed Nov. 24, 1972, now abandoned, which is a continuation-in-part application of co-pending U.S. application Ser. No. 232,966, filed Mar. 8, 1972, now issued to U.S. Pat. No. 3,787,423.

This invention relates to a new class of heterocyclic methyl esters and N-(lower alkanesulfonyl) or N-(sulfo-lower alkyl)amides of (3-trifluoromethylphenoxy)-(4-chlorophenyl)acetic acid and to the non-toxic, pharmacologically acceptable acid addition salts of the basic heterocyclic compounds and alkali metal salts of the sulf-substituted compounds which compounds have hypocholesterolemic activity and thus are useful in the treatment of atherosclerosis, as well as blood platelet aggregating inhibiting activity, which is useful in the prevention of thrombosis.

Clinical studies show that cholesterol apparently plays a major role in the formation of atherosclerotic plaques by accelerating the deposition of blood lipids on the arterial wall. The purpose of this invention is to disclose a new class of chemical compounds which effectively reduce the concentration of cholesterol, triglycerides and other lipids in blood serum and thus ameliorate the condition usually associated with lipid deposition.

The heterocyclic methyl esters and the N-(lower-alkanesulfonyl) and N-(sulfo-lower alkyl)amides of (3-trifluoromethyl)(4-chlorophenyl)acetic acids of this invention are compounds having the following structural formula:

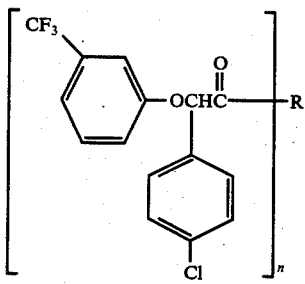

I wherein R is a heterocyclic methoxy radical including pyridylmethoxy, for example, 3-pyridylmethoxy and the like, halo-substituted pyridylmethoxy, for example, 5-fluoro-3-pyridylmethoxy, 5-chloro-3-pyridylmethoxy, 6-chloro-3-pyridylmethoxy and the like, methyl substituted pyrazolylmethoxy, for example, 5-methyl-3-pyrazolylmethoxy and the like, halo-substituted isoxazolylmethoxy, for example, 5-chloro-3-isoxazolylmethoxy and the like, methyl substituted isoxazolylmethoxy, for example 5-methyl-3-isoxazolylmethoxy and the like, 2-methyloxazolinyl-4,4-dimethoxy, lower alkanesulfonylamino such as methanesulfonylamino, ethanesulfonylamino and the like, or sulfo-lower alkyl amino such as sulfoethylamino, sulfopropylamino and the like, and n is an integer of one except when R is 2-methyloxazolinyl-4,4-dimethoxy when n is an integer of two.

A preferred embodiment of this invention relates to compounds selected from the following formulae:

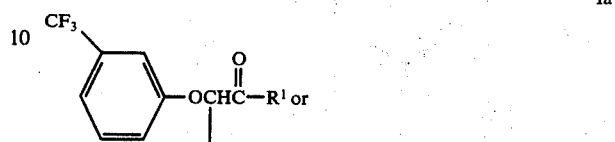

wherein $R^1$ is 3-pyridylmethoxy, 2-sulfoethylamino or 3-sulfopropylamino. This group of compounds are particularly good hypocholesterolemic and hypolipemic compounds.

Included within the scope of this invention are the non-toxic, pharmacologically acceptable acid addition salts and the non-toxic, pharmacologically acceptable alkali metal salts of the instant products (I) which may be prepared by treating the products with an acid having a pharmacologically acceptable anion or with an alkali metal base, respectively. In general, any acid or base which will not cause an adverse physiological effect when ingested by the body system is considered as being within the scope of this invention; suitable acids include inorganic acids such as hydrochloric acid, hydrobromic acid, sulfuric acid, phosphoric acid and the like and organic acids such as acetic acid, propionic acid, butyric acid, citric acid, tartaric acid and the like. Suitable alkali metal bases include sodium hydroxide, potassium hydroxide and the like.

The (3-trifluoromethylphenoxy)(4-chlorophenyl)acetates and acetamides (I) are prepared by the reaction of a (3-trifluoromethylphenoxy)(4-chlorophenyl)acetyl halide with either a hydroxymethyl heterocyclic, an alkali metal salt of an alkanesulfonamide or an amino lower alkanesulfonic acid. The following equation illustrates this reaction:

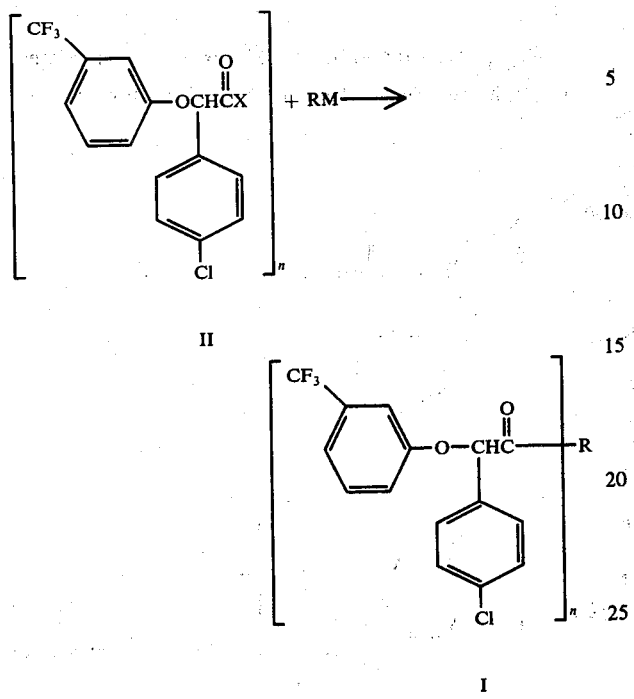

wherein R and *n* are as defined above; X is halo, for example, chloro, bromo and the like and M is hydrogen or a cation derived from an alkali metal such as the cation derived from sodium and the like.

The reaction is conducted in a solvent which is inert or substantially inert to the reactants employed. Suitable solvents include tetrahydrofuran, diethyl ether, dimethylformamide, dioxane, chloroform, pyridine, triethylamine and the like. The process is conducted over a temperature range of from about −25° C. to ambient temperature with the initial mixing preferably occurring at a temperature in the range of from about −25° C. to 0° C. and then continuing the reaction at a temperature in the range of 0° C. to ambient temperature.

When taurine or homotaurine is employed, it is preferred to prepare their alkali metal salt in situ and to employ a slight excess of base to react with the hydrohalic acid produced in the reaction.

The following examples illustrate the novel products of this invention and the manner in which they may be prepared. The examples are illustrative only and it will be apparent to those skilled in the art that other reactants and reagents similar to those described in the examples may be employed to afford similar products.

EXAMPLE 1

3-Pyridylmethyl (3-Trifluoromethylphenoxy)(4-chlorophenyl)acetate Hydrochloride

Step A: (3-Trifluoromethylphenoxy)(4-chlorophenyl)acetyl Chloride

Thionyl chloride (44.5 g., 0.375 mole) is added over a five-minute period to a suspension of (3-trifluoromethylphenoxy)(4-chlorophenyl)acetic acid (100 g., 0.30 mole) in 125 ml. of chloroform. The mixture is stirred at room temperature for 30 minutes and then heated under reflux for six hours. As soon as the temperature reaches the boiling point a clear homogenous solution results. At the end of the reaction period, the solvent and volatile reaction products are removed by evaporation in vacuo. High purity (3-trifluoromethylphenoxy)(4-chlorophenyl)acetyl chloride (105 g.) is obtained as a residual oil in almost theoretical yield.

Step B: 3-Pyridylmethyl (3-Trifluoromethylphenoxy)(4-chlorophenyl)acetate hydrochloride A solution of 3-pyridylcarbinol (5.7 g., 0.0522 mole) in triethylamine (144 ml., 0.13 mole) is cooled to −15° C. To this solution is added (3-trifluoromethylphenoxy)(4-chlorophenyl)acetyl chloride (18 g., 0.0515 mole) in ether (25 ml.). The reaction mixture is stirred for four hours at −5° C. and then at room temperature for 4 hours. The reaction mixture is filtered and the filtrate is washed successively with water, dilute sodium bicarbonate and then water until neutral. The ether solution is dried over magnesium sulfate filtered and to this solution is added ethanolic HCl. An oil separated which slowly crystallized. The solid is collected and recrystallized from a mixture of of isopropanol (30 ml.) and ether (30 ml.) to afford 8.6 g. of product. A small sample recrystallized for analysis has a melting point of 147°–149° C.

Elemental analysis for $C_{21}H_{15}ClF_3NO_3 \cdot HCl$: Calc.: C, 55.04; H, 3.52; N, 3.06; Found: C, 54.81; H, 3.41; N, 3.01.

EXAMPLE 2

4,4-Bis [(3-Trifluoromethylphenoxy)(4-chlorophenyl)acetoxymethyl]-2-methyloxazoline To a solution of 2-methyl-4,4-dihydroxymethyloxazoline (0.1 mole) in pyridine (25 ml.) is added a solution of (3-trifluoromethylphenoxy)(4-chlorophenyl)acetyl chloride (0.2 mole) in ether (25 ml.). The reaction mixture is stirred for five hours at −5° C. and then at room temperature for two hours. The reaction mixture is filtered and the filtrate washed successively with water, dilute sodium bicarbonate and then water until neutral. The ether solution is dried over magnesium sulfate, filtered and the solvent removed to afford 4,4-bis [(3-trifluoromethylphenoxy)(4-chlorophenyl)acetoxymethyl]-2-methyloxazoline.

EXAMPLE 3

N-(2-Sulfoethyl)(3-Trifluoromethylphenoxy)(4-chlorophenyl)acetamide Sodium Salt

To a solution of 2-aminoethanesulfonic acid (5.38 g., 0.043 mole) in water (50 ml.), sodium hydroxide (1 N, 43 ml.) and tetrahydrofuran (30 ml.) at 5° C. is added a solution of (3-trifluoromethylphenoxy)(4-chlorophenyl)acetyl chloride (15.0 g., 0.043 mole) in tetrahydrofuran (30 ml.). The solution of the acid chloride is added in 1 ml. portions alternating with the addition of 1 ml. portions of sodium hydroxide (1 N). This addition is conducted at a temperature between 2°–6° C. over a one hour period. The reaction mixture is allowed to stand overnight at room temperature. The solvents are removed under vacuum and the residue is treated with isopropyl ether and the insoluble material removed by filtration. The filtrate is concentrated under reduced pressure and the residue is crystallized from a mixture of n-butyl chloride (1 part), methylcyclohexane (6 parts) and petroleum ether (5 parts) to afford substantially pure product, melting point 175°–180° C. with decomposition and preliminary softening at 135° C.

Elemental analysis for $C_{17}H_{14}ClF_3NaNO_5S\cdot H_2O$: Calc.: C, 42.73; H, 3.37; N, 2.93; Found: C, 42.73; H, 3.18; N, 3.17.

The free acid is obtained by treating the sodium salt with an equivalent amount of dilute hydrochloric acid. By substituting for the 2-aminoethanesulfonic acid employed above in Example 3, an equimolar quantity of 3-aminopropane sulfonic acid and following substantially the procedure described therein there is obtained N-(3-sulfopropyl)-(3-trifluoromethylphenoxy)(4-chlorophenyl)acetamide, sodium salt.

EXAMPLE 4

N-Methanesulfonyl (3-trifluoromethylphenoxy)(4-chlorophenyl)acetamide (3-Trifluoromethylphenoxy)(4-chlorophenyl)acetyl chloride (0.02 mole) in tetrahydrofuran (50 ml.) is added over a 15-minute period to a solution of the sodium salt of methanesulfonamide (2.5 g., 0.021 mole) in tetrahydrofuran (50 ml.) at 0°–5° C., under a nitrogen atmosphere. The mixture is stirred at 20° C. for 20 hours and then the solvent is evaporated under vacuum. The residue is dissolved in chloroform and the solution is extracted with water. The chloroform solution is dried over anhydrous magnesium sulfate, filtered and the solvent removed to afford N-methanesulfonyl (3-trifluoromethylphenoxy)(4-chlorophenyl)acetamide.

In a manner similar to that described in Example 1 for the preparation of 3-pyridylmethyl (3-trifluoromethylphenoxy)(4-chlorophenyl)acetate hydrochloride all of the esters of this invention may be prepared. By substituting for the 3-pyridylcarbinol of Example 1, Step B, another hydroxymethyl substituted heterocyclic and by following substantially the procedure described therein, all of the heterocyclic methyl esters of the invention may be obtained. The following equation together with Table I depict the products which may be obtained:

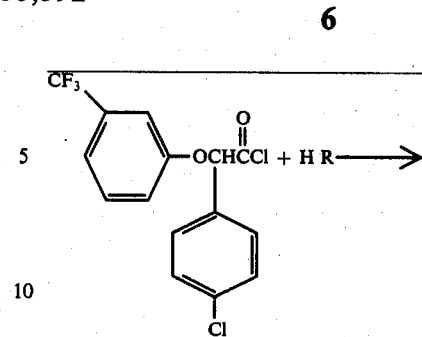

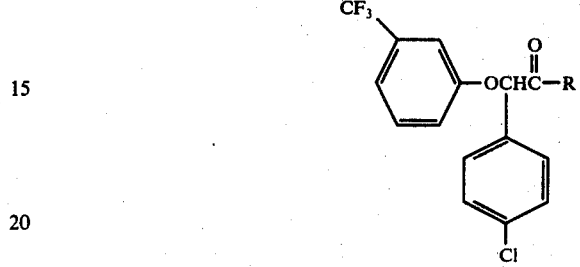

Table I

| Example No. | R |
|---|---|
| 5 | —OCH$_2$-(3-fluoro-5-pyridyl) |
| 6 | —OCH$_2$-(3-chloro-5-pyridyl) |
| 7 | —OCH$_2$-(6-chloro-3-pyridyl) |
| 8 | —OCH$_2$-(3-methyl-1H-pyrazol-5-yl) |
| 9 | —OCH$_2$-(3-methylisoxazol-5-yl) |

What is claimed is:
1. A compound of the formula:

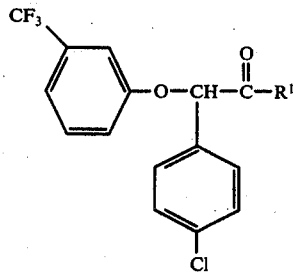

wherein $R^1$ is sulfo-lower alkyl amino or the non-toxic, pharmacologically acceptable alkali metal salts.
2. A compound according to claim 1 wherein $R^1$ is 2-sulfoethylamino.
3. A compound according to claim 1 wherein $R^1$ is 3-sulfopropylamino.

* * * * *